US00PP27128P2

(12) United States Plant Patent
Beckman et al.

(10) Patent No.: US PP27,128 P2
(45) Date of Patent: Sep. 6, 2016

(54) PEACH TREE NAMED 'GULFATLAS'

(50) Latin Name: ***Prunus persica* (L.) Batsch**
Varietal Denomination: GulfAtlas

(71) Applicants: The United States of America as represented by the Secretary of Agriculture, Washington, DC (US); The University of Georgia Research Foundation, Athens, GA (US); The University of Florida, Gainesville, FL (US)

(72) Inventors: Thomas G Beckman, Warner Robins, GA (US); Jose X Chaparro, Gainesville, FL (US); Patrick J Conner, Tifton, GA (US)

(73) Assignees: The United States of America, as represented by the Secretary of Agriculture, Washington, DC (US); The University of Georgia Research Foundation Inc., Athens, GA (US); The University of Florida, Gainesville, FL (US)

( * ) Notice: Subject to any disclaimer, the term of this patent is extended or adjusted under 35 U.S.C. 154(b) by 0 days.

(21) Appl. No.: 13/998,066

(22) Filed: Sep. 27, 2013

(51) Int. Cl.
*A01H 5/08* (2006.01)

(52) U.S. Cl.
USPC ..... Plt./197

(58) Field of Classification Search
USPC ..... Plt./197
See application file for complete search history.

*Primary Examiner* — Anne Grunberg
(74) *Attorney, Agent, or Firm* — John D. Fado; Gail E. Poulos

(57) ABSTRACT

A new and distinct variety of peach tree, denominated 'GulfAtlas', has a winter chilling requirement estimated at approximately 400 chill units (cu). The tree is medium size, moderately vigorous, and semi-spreading in growth habit. It bears showy, pink flowers, and leaves with reniform glands. Trees of 'GulfAtlas' are self-fertile and regularly bear heavy annual crops. Fruit are uniformly firm and have yellow, non-melting flesh. Fruit are nearly round, and uniform with substantially symmetrical shape, and have an attractive approximately 75% red skin. The fruit of 'GulfAtlas' typically ripen about 3 weeks after 'Gulfcrimson' in midJune at Attapulgus, Ga.

3 Drawing Sheets

Latin name of the genus and species of the plant claimed: 'GulfAtlas' is a peach tree that is *Prunus persica* (L.) Batsch.

Variety denomination: The new peach tree claimed is of the variety denominated 'GulfAtlas' *Prunus persica*. (L.) Batsch.

BACKGROUND OF THE INVENTION

The present invention relates to a new and distinct variety of peach [*Prunus persica* (L.) Batsch] tree adapted to a subtropical (moderate chill) winter climate. This new variety, named 'GulfAtlas', produces highly colored, good eating quality, cling-stone and non-melting flesh fruit for fresh market in mid-June at Attapulgus, Ga. Contrast is made to 'Gulfcrimson' peach (U.S. Plant Pat. No. 20,174), a standard variety, for reliable description. 'GulfAtlas' is a promising candidate for commercial success in that it has large, attractive red skin, sweet fruit that ripens evenly.

'GulfAtlas' peach tree (genotype) originated in a cultivated area of the fruit breeding program at the University of Georgia, located at Attapulgus, Ga. where it was tested. The seed parent was Flavorcrest (unpatented) and the pollen parent was FL98-10C (unpatented, and of complex origin). 'GulfAtlas' was selected in 2003 because it exhibited yellow, non-melting flesh, in a large fruit with a bright red skin. It was designated and tested as AP03-22. It was asexually propagated by budding onto 'Flordaguard' (unpatented) seedling rootstock (for rootknot nematode control) and determined to have unique tree and fruit characteristics making it worthy for commercial fresh fruit production. Trees were budded at the USDA-ARS, SE Fruit and Nut Research Laboratory in Byron, Ga. and transplanted to the evaluation site at the University of Georgia Research and Extension Center in Attapulgus, Ga. There are no known effects of this standard rootstock on this scion cultivar. Asexually propagated plants remained true to the original tree and all characteristics of the tree and the fruit have transmitted for 2 generations. 'GulfAtlas' differs from its seed parent, 'Flavorcrest', in that 'Flavorcrest' requires approximately 750 chill hours and 'GulfAtlas' requires 400, ripens ca. 100 days from bloom and 'GulfAtlas' requires ca. 120, has melting flesh and 'GulfAtlas' is non-melting and is freestone and 'GulfAtlas' is clingstone. 'GulfAtlas' differs from its pollen parent, 'FL98-10C', in that 'FL98-10C' requires less chilling , approximately 250 chill hours and ripens in a shorter time, approximately 92 days, from bloom.

SUMMARY OF THE INVENTION

The new and distinct variety of peach tree bears fruit that ripen in mid-June at Attapulgus, Ga., and has a moderately low chilling dormancy requirement. 'GulfAtlas' typically blooms 3 days before 'Gulfcrimson' peach in mid-February at Attapulgus, Ga. The estimated chilling requirement is approximately 400 chill units, based on bloom time. 'GulfAtlas' tree has fruit that are clingstone and of good flavor and eating quality. The trees are vigorous, productive and without alternate bearing. Trees attain in two years, a height of approximately two meters and a spread of one and a half meters at Attapulgus, Ga. Terminal growth of up to half meter annually is common on mature 5-year-old trees with normal pruning to a vase shape.

The first fruit ripen in mid-June at Attapulgus, Ga. or in about 120 days from full bloom, typically about three weeks after 'Gulfcrimson' ripens. The fruit are uniformly larger than 'Gulfcrimson', averaging nearly about 200 g when properly thinned to a full crop. Additionally, 'GulfAtlas' fruit are more round and slightly larger diameter than 'Gulfcrimson' which has longer fruit. Ripe fruit have averaged approximately 75% red skin. There is some red pigmentation in the flesh at the pit. The flowers anthers are yellow, and leaf glands are reniform, common characteristics of many standard peach varieties. No buttons (parthenocarpy fruit) have been observed.

BRIEF DESCRIPTION OF THE PHOTOGRAPHS

The accompanying drawings are color photographs which show a typical specimen of the fruit, leaf, and stem (FIG. 1), typical flower (FIG. 2) and typical tree (FIG. 3) of the new variety as nearly true as it is reasonably possible to make in a color illustration of this type.

DETAILED BOTANICAL DESCRIPTION

Figure 1:
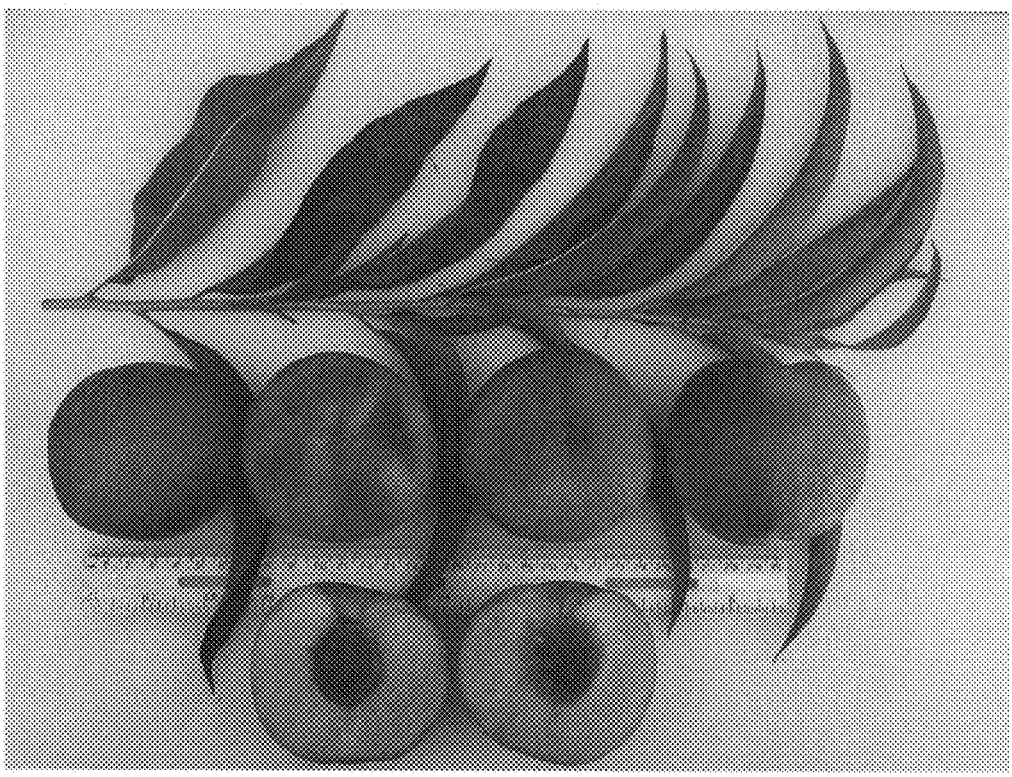
FIG. 1 shows an attractive shape and exterior coloration of 6 specimens of fruit above a ruler in side view, stem end view, a blossom end view, a side view showing the suture and a fruit cut longitudinally to show with and without the pit.
Figure 2:
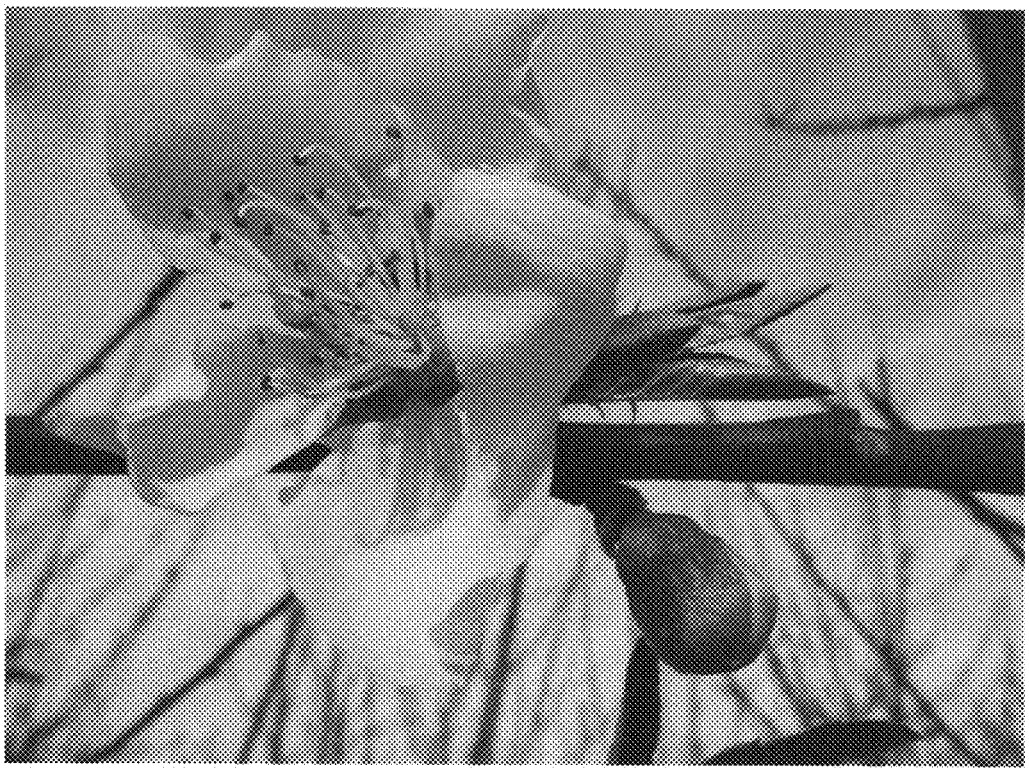
FIG. 2 shows a typical showy flower of the new variety.
Figure 3:
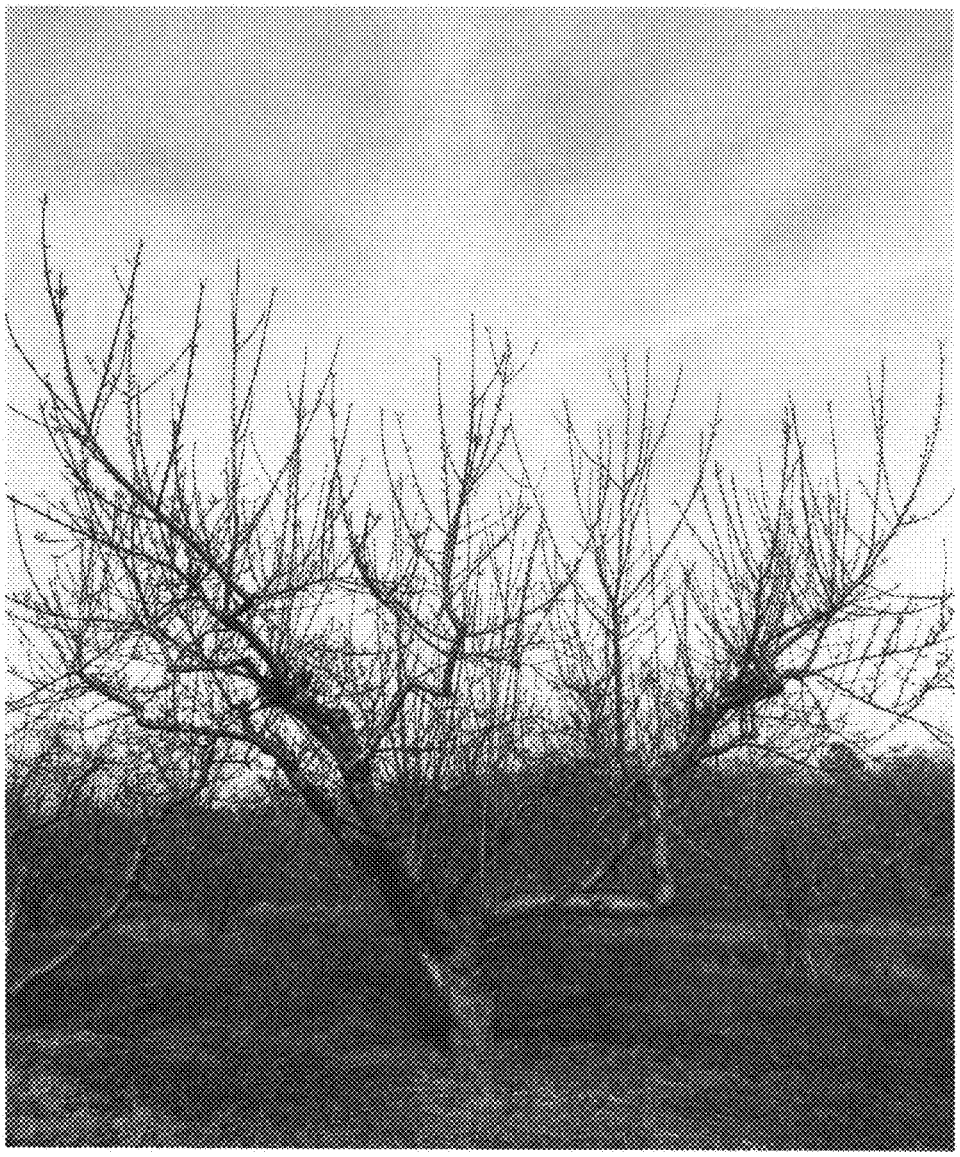
FIG. 3 shows the typical semi-spreading architecture of an 8 year-old tree of the new variety.

The tree, flowers, and fruit may vary in slight detail due to variations in soil type, cultural practices, and climatic conditions. The potential for commercial production of fresh fruit by 'GulfAtlas' is high, due to its attractive red skin over a bright yellow ground color, large fruit of good flavor, and good firmness with even ripening throughout the fruit. The present botanical description is that of the variety grown on 6-year-old trees on 'Flordaguard' rootstock under the ecological conditions at Attapulgus, Ga. Colors (except in common terms) are described from "The Pantone Book of Color", published by H. N. Abrams, Inc., N.Y. 1990.

Tree:

*Ploidy*.—Diploid.

*Size*.—Trees are medium stature when trained to an open vase form Vigor. — Moderately vigorous, and must be summer and winter pruned when grown to a vase shape to keep the tree open to get strong fruiting wood in the lower center. Trees respond typically to irrigation and fertilization. Tree growth of approximately 1.5 to 2 meters in height and width occurs the first growing season in the field at Attapulgus, Ga.

*Density*.—Light to medium in branching habit. Pruning is required to open the tree center to promote sunlight entrance for enhancing fruit color and sugar.

*Form*.—Semi-spreading, but easily pruned to vase shape.

*Hardiness*.—Hardy with respect to typical Georgia winters.

*Bearer*.—Productive annually without alternate bearing observed. Trees are self fertile and must be fruit thinned to avoid limb breakage and obtain large fruit size. Trees often set several times the number of fruit needed for a full crop load. Trees bear on both spurs and long shoots. Average length of spurs is approximately 6.5 mm.

*Chilling requirement*.—Estimated endodormancy chilling requirement is approximately 400 chill units based on time of bloom and leafing in relation to standard varieties.

Trunk:

*Size*.—Medium trunk diameter attaining approximately 14 cm diameter at a height of approximately 20 cm at the end of 5 years growth at Attapulgus, Ga.

*Texture*.—Medium smooth, but changes to light shaggy as tree ages.

*Bark color*.—Older bark gray, Chinchilla (Pantone 17-1109).

*Lenticels*.—Moderately low number, approximately 4 to 6 per approximately 4 square inches of surface area of trunk; and medium length, approximately 16 to approximately 20 mm perpendicular to the trunk. Color is grey, Sponge, Pantone 15-1344.

Branches:

*Size*.—Strong growth of scaffold branches. Fruiting branches are mostly large diameter, approximately 7 to approximately 9 mm, and not overly twiggy, resulting in strong fruiting wood. Thus, the tree growth and structure permits easier and faster winter pruning.

*Texture*.—Relatively smooth, numerous lenticels but smaller size than found on trunk and old scaffolds. Roughness increases with age.

*Color*.—New wood is light green, Celery Green Pantone 13-0532; old wood is brown, Clove Pantone 18-1320.

*Crotch angles*.—Angles are selected at approximately 45 to near approximately 90 degrees in first year of tree training. Natural angles are within the normal range of standard varieties for a semi-spreading tree.

Leaves:

*Size*.—Medium, approximately 15 to 17 cm length, including the petiole; approximately 38 to approximately 44 mm width.

*Thickness*.—Regular and average for commercial varieties. Not noticeably unusual.

*Form*.—Lanceolate.

*Apex*.—Acute.

*Margin*.—Serrulate, slightly undulate.

*Base*.—Cuneate.

*Surface*.—Upper, glabrous; Lower, medium large veins that are pinnately netted.

*Color*.—Lower surface is green, Peridot Pantone 17-0336. Upper leaf surface is Elm Green, Pantone 18-0121. Leaf vein is Green Oasis Pantone 15-0538.

*Glands*.—Usually 2, small reniform glands mostly on lower leaf blade, but occasionally on petiole. Leaf glands on young leaves are light green, Leek Green Pantone 15-0628. Size averages about 1 in length and about 0.3 mm in width.

*Petiole*.—About 1 cm, approximately 0.8 to approximately 1.1 cm.; approximately 1.3 mm in diameter. Light green, Cedar Pantone 16-0526.

*Stipules*.—Medium, equal to most commercial peach varieties, usually about 2 per bud, and abscising just before leaf becomes full size in summer growth. Color at full size is green, Piquant Green Pantone 17-0235, but tinged at its base with anthocyanin. Flame Pantone 17-1462 before abscising.

*Leaf blade incisions*.—Serrulate and slightly undulate.

*Arrangement*.—Alternate.

Flower buds:

*Hardiness*.—Hardy with respect to south Georgia winters, approximately 15 degrees F. observed.

*Abundance*.—Very high due to shorter than average internode length. Most buds set fruit in absence of spring frosts and show little evidence of bud drop.

*Size*.—Medium, average approximately 5 mm length in mid-winter.

*Form*.—Plump, conic and free.

*Vegetative bud shape*.—Vegetative bud apex is acute.

*Vegetative bud size*.—Average length of buds is approximately 5.6 mm with an average diameter of approximately 2.1 mm.

*Position of vegetative bud to* 1 *year old shoot*.—Vegetative buds are held slight out from 1 year old shoot.

*Surface*.—Pubescent scales.

*Color*.—Brown, Stucco Pantone 16-1412, in late summer.

Flowers:

*Blossom period*.—Typically blooms 3 days before 'Gulfcrimson' peach-averages about 70% bloom February 18$^{th}$ at Attapulgus, Ga., but occurring over an approximately 7-10 day period. Time and length of bloom are dependent on ambient temperature.

*Aroma*.—Not detectable.

*Flower density*.—Abundant, varying approximately 1 to approximately 2 per node at the base of the flowering shoot, but usually 1 at the distal end of the flowering shoot.

*Type*.—Showy, location and seasonally variable within the range of commercial showy varieties. Average flower diameter-approximately 4.6 cm. Average petal lengths, approximately 21 mm; width approximately 16 mm. Texture smooth. Margins are undulate and smooth.

*Color*.—Orchid Pink, Pantone 13-2010 at flower opening.

*Flower parts*.—Stamens and pistil size, shape and color are within the range of standard commercial varieties. There are 5 sepals and petals. Sepals average approximately 5 mm length and approximately 5 mm wide at attachment to calyx cup and rounded at the distal end. Sepals are green, Spinach Pantone 16-0439, on the interior and red, Cardinal Pantone 18-1643, on the exterior with a smooth pubescent margin. Sepals are pubescent and petals are glabrous. Pistils are usually 1 per flower and straight, without curls or curves, just prior to flower opening. Pistil length from tip of stigma to base of ovary averages approximately 15 mm. Pistils are light green, Pale Star Pantone 12-0626. Flower pedicel is approximately 2 mm length.

*Flower arrangement of petals*.—Petals slightly overlap, approximately 10% of petal width, at dehiscence.

*Calyx up*.—Medium small in the size range of commercial varieties. Calyx cup diameter is approximately 7 mm at the top, at the time of flower opening. Calyx cup exterior is red, Garnet Pantone 19-1655, and interior of the cup base is orange, Persimmon Orange Pantone 16-1356.

*Stamen*.—Anthers are yellow, Cornsilk Pantone 13-0632, at flower opening. Number of anthers varies from about 35 to about 40 and filament length is approximately 7 to approximately 9 mm. Filaments are whitish, Water Lily Pantone 11-0304, at flower opening, lengthening to approximately 14 to approximately 16 mm at anther dehiscence and darkening to Raspberry Wine Pantone 18-1741.

*Pollen*.—Abundant and bright yellow, Snapdragon Pantone 13-0840.

*Fertility*.—Fully self fertile, and no cross pollination is required. Fruit set is abundant.

Fruit:

*Maturity when described*.—Tree ripe, Jun. 29, 2010 at Attapulgus, Ga. Size. — Uniform, medium large, large size for early mid-season maturity at approximately 130 to 150 grams. Varies with fruit number per tree, soil type, climatic conditions and cultural practices. Average equatorial diameter approximately 2⅝ inches or approximately 66 mm. Average polar length, stem to distal end, is approximately 2½ inches or approximately 64 mm.

*Penduncle size and color*.—Length averages approximately 5 mm; Width is approximately 3 mm. Color is green, Cedar Pantone 16-0526.

*Longitudinal section form*.—Slightly squat.

*Transverse section through diameter*.—Mostly round.

*Suture*.—Slightly ridged from stem to distal end. A slight crease at stem end of fruit.

*Ventral surface*.—Usually rounded.

*Shape of fruit base*.—Slightly cordate.

*Apex*.—Usually rounded to slightly obtuse.

*Crater at stem attachment*.—Flaring oval to the suture. Depth is 12 to 15 mm; breadth is 15 mm at top and 5 mm at pedicel attachment.

Skin:

*Thickness*.—Medium in comparison to commercial peach varieties.

*Texture*.—Medium in comparison to standard varieties.

*Tenacity*.—Tenacious to flesh.

*Color*.—Red, Salmon Red Pantone 15-1626, over approximately 80% to approximately 100% of skin. Ground color is yellow, Snapdragon Pantone 13-0840. Fruit exposed to sunlight have a higher Degree of enhanced red skin.

*Tendency to crack*.—None observed.

*Taste*.—No astringency observed.

*Epidermis*.—Pubescent and about the same as 'Gulfcrimson'.

Flesh:

*Ripens*.—Evenly within each fruit.

*Texture*.—Firm, juicy, non-melting when fully ripe.

*Fibers*.—Very fine, small, tender, and abundant.

*Aroma*.—Moderate and in the middle range of commercial peach varieties.

*Eating quality*.—Good, moderately sweet, slightly acid. Soluble solids average 11.2 brix, Approximately 2.8 penetrometer firmness with a standard about 5.16 inch tip following a seven day post-harvest storage protocol.

*Juice*.—Moderately abundant, slightly more than Gulfcrimson.

*Color*.—Bright yellow, Snapdragon Pantone 13=0840. There is red, Chrysanthemum Pantone 17-1641 at the pit, but no red in the flesh.

*Browning by oxidation*.—Not detectable on tree ripe fruit beginning to soften.

*Amygldalin*.—Undetected.

*Texture*.—Smooth as found in 'Gulfcrimson'.

Stone:

*Type*.—Clingstone.

*Size*.—Medium large: average length is approximately 34 mm; average width is approximately 27 mm; average thickness is approximately 17 mm; average wall thickness is approximately 5 mm.

*Color*.—Red, Baked Apple Pantone 18-1648 when flesh is freshly cut.

*Form*.—Oblong.

*Base*.—Straight.

*Apex*.—Slightly acute.

*Sides*.—Near equal.

*Surface*.—Regularly furrowed toward the ventral edge, smooth on dorsal edge and lightly pitted from base to apex.

*Tendency to split*.—None observed.

*Seed*.—Bitter kernel, amygdalin is abundant. Viable if stratified upon removal from fruit at harvest, and without drying. Kernel is yellow, Pale Banana Pantone 12-0824, when first removed from ripe fruit. Seed is approximately 19 mm in length, approximately 1.1 mm wide and approximately 5 mm thick. Shape is acute tip with obtuse base and overall ovate shape.

Use: Fresh, dessert.

Resistance to disease: High resistance to bacterial spot incited by *Xanthomnonas campestris* pv. Pruni Pruni (Pers.) Diet. No unusual resistance or susceptibility to insects and diseases noted.

Keeping quality: Excellent after about 10 days at approximately 2 degrees C. and with minimal bruises or scarring appearing on skin.

Shipping quality: Degree of firmness at harvest and firmness retained in refrigeration for approximately 10 days at approximately 2 degrees C., with no internal breakdown of flesh or appreciable loss of eating quality, indicates fruit should be highly acceptable for shipping.

We claim:

1. A new and distinct peach tree as illustrated and described, characterized by a moderate chilling requirement, and bearing fruit having firm, yellow, and non-melting, clingstone, and smooth textures flesh of good eating quality and an attractive, high percentage red skin with fruit ripening in mid-June, typically three weeks after 'Gulfcrimson' at Attapulgus, Ga.

* * * * *